United States Patent [19]

Schweizer et al.

[11] 3,947,441

[45] Mar. 30, 1976

[54] SUBSTITUTED 2-AMINO-4-(HYDROXYAMINO)-PYRIMIDINES

[75] Inventors: Ernst Schweizer, Basel; Jörg Frei, Schonenbuch; Atso Ilvespää, Allschwil, all of Switzerland

[73] Assignee: Ciba-Geigy Corporation, Ardsley, N.Y.

[22] Filed: Aug. 20, 1974

[21] Appl. No.: 498,906

[30] Foreign Application Priority Data
Aug. 24, 1973 Switzerland.................. 12198/73
July 10, 1974 Switzerland................... 9507/74

[52] U.S. Cl.................. 260/256.4 N; 260/256.4 C; 260/256.5 R; 424/251
[51] Int. Cl.².................................... C07D 239/42
[58] Field of Search............................ 260/256.4 N

[56] References Cited
UNITED STATES PATENTS
3,513,185    5/1970    Cresswell et al............. 260/256.4 N

*Primary Examiner*—Richard J. Gallagher
*Assistant Examiner*—James H. Turnipseed
*Attorney, Agent, or Firm*—Joseph G. Kolodny; John J. Maitner; Theodore O. Groeger

[57]                ABSTRACT

Cpmpounds of the class of 5-substituted and 5,6-disubstituted 2-amino-4-(hydroxyamino) and 2,4-bis-(hydroxyamino)pyrimidines and their pharmaceutically acceptable acid addition salts possess valuable biological properties, in particular antibacterial and antimalarial activity and potentiate the action of antibacterial sulphanilamide derivatives. Specific embodiments are 2-amino-4-(hydroxyamino)-5-(3,4,5-trimethoxybenzyl)-pyrimidine, and 2-amino-4-(hydroxyamino)-5-(p-chlorophenyl)-6-ethyl pyrimidine and its hydrochloride.

8 Claims, No Drawings

SUBSTITUTED 2-AMINO-4-(HYDROXYAMINO)-PYRIMIDINES

DETAILED DESCRIPTION

The present invention relates to new pyrimidine derivatives having valuable biological properties, and to the pharmaceutical preparations and combinations of pharmaceutical preparations containing the new compounds.

The new pyrimidine derivatives of the invention correspond to the formula I

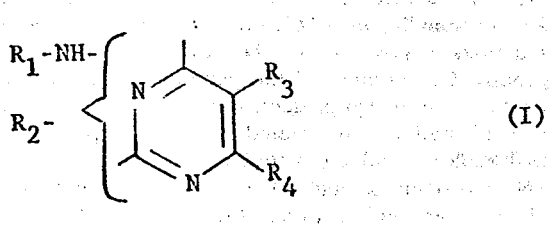

wherein
$R_1$ represents hydroxy or protected hydroxy,
$R_2$ represents amino, hydroxy, hydroxyamino or protected hydroxyamino,
$R_3$ represents aryl or aralkyl which are unsubstituted or substituted and are at most binuclear, and
$R_4$ represents hydrogen or a lower alkyl group.

The invention relates likewise to the addition salts of compounds of the general formula I whith inorganic and organic acids, in particular to the pharmaceutically acceptable acid addition salts.

In the new pyrimidine derivatives, a protected hydroxy group $R_1$, as well as a protected hydroxy group optionally present in $R_2$, is, for example, a group that can be split in an acid medium, e.g. a tertiary alkoxy group, such as the 1,1,2,2-tetramethylpropoxy group or the tert.butoxy group, a lower 1-alkoxyalkoxy group, or an analogous cyclic group i.e. a cyclic group likewise having two oxygen atoms bound to the same carbon atom, e.g. a 1-ethoxyethoxy group or 1-butoxyethoxy group, or a 4-methoxytetrahydropyran-4-yloxy group, 4-methoxytetrahydrothiopyran-4-yloxy group or 1,1-dioxo-4-methoxytetrahydrothiopyran-4-yloxy group, a tetrahydrofuran-2-yloxy group and, in particular, a tetrahydropyran-2-yloxy group, or a group that can be split in a weakly basic medium, such as the methoxyacetoxy group.

Furthermore, a protected hydroxy group $R_1$, as well as a protected hydroxy group optionally present in $R_2$, can also be a group that can be split by hydrogenolysis, such as a monoarylmethoxy group or diarylmethoxy group, e.g. the benzyloxy group, or a benzyloxy group carrying inert substituents, or the diphenylmethoxy group. Inert substituents of a benzyloxy group particular, 1 are, in paraticular, lower alkyl and lower alkoxy groups, such as the methyl group and the methoxy group.

The symbol $R_3$ denotes, for example, a 1-naphthyl, 2-naphthyl, phenethyl, α-methylphenethyl, 3-phenylpropyl, 4-phenylbutyl, (1-naphthylmethyl) or (2-naphthylmethyl) group and, in particular, a phenyl or benzyl group. These groups, especially the two last-mentioned groups, can be substituted by, for example, one to four substituents from the series of halogen atoms up to atomic number 35, alkyl, alkoxy or 1-hydroxyalkyl groups each having at most 4 carbon atoms, hydroxy groups, trifluoromethyl groups and methylenedioxy groups, whereby preferably at most two hydroxy groups or trifluoromethyl groups, or at most one methylenedioxy group, are present, on their own or in addition to any of the other above-mentioned substituents. Halogen atoms up to atomic number 35 are fluorine, bromine and, in particular, chlorine atoms, alkyl, alkoxy and 1-hydroxyalkyl groups having at most 4 carbon atoms are, e.g. ethyl, isopropyl, tert.butyl, ethoxy, propoxy, isopropoxy, butoxy, 1-hydroxyethyl or 1-hydroxybutyl groups, and especially methyl, methoxy or hydroxymethyl groups. There may be mentioned as an example of a monosubstituted radial $R_3$ the p-chlorophenyl group, of a di-substituted radical $R_3$ the 3,4-dimethoxybenzyl group, of a tri-substituted radical $R_3$ the 3,4,5-trimethoxybenzyl group, and of a tetra-substituted radical $R_3$ the 2,3,4,5-tetramethoxybenzyl group; but radicals $R_3$ can equally well be other aryl or aralkyl groups that are at most binuclear, particularly phenyl or benzyl groups, which carry one or more, preferably up to three, of the above-mentioned substituents, the carried substituents being either identical or different. As a lower alkyl group, $R_4$ is one having at most 6 carbon atoms, preferably at most 4 carbon atoms, for example, a propyl or butyl group and especially a methyl or ethyl group.

The compounds of the general formula I and their acid addition salts are prepared according to the invention by a process wherein a compound of the general formula II

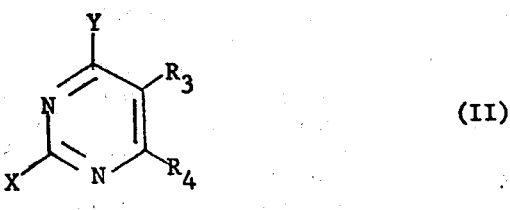

wherein
one of the symbols X and Y represents an exchangeable radical, and the other an exchangeable radical or an amino or hydroxy group,
and $R_3$ and $R_4$ have the meaning given under formula I, is reacted with a compound of the general formula III $$R_1 - NH_2 \quad (III),$$

wherein $R_1$ has the meaning given under formula I, in an amount sufficient for the replacement of at least one of the exchangeable radicals X and Y, and a reaction product, in which there is still an exchangeable radical X or Y present, is again reacted with a compound of the general formula III, or is converted by reaction with ammonia, or by partial hydrolysis, into a compound of the general formula I having an amino group or hydroxy group $R_2$, and, optionally, in a compound of the general formula I wherein $R_1$ is a protected hydroxy group and, optionally, $R_2$ is a protected hydroxyamino group, while $R_3$ and $R_4$ have the meaning given under formula I, the hydroxy group and, where the case applies, the hydroxyamino group are liberated, and/or, optionally, a resulting compound of the general formula I is converted into an addition salt with an inorganic or organic acid.

In the starting materials of the general formula II, exchangeable radicals X and/or Y are, for example, halogen atoms, such as bromine and particularly chlorine, or lower alkylthio and alkylsulphonyl groups such as the methylthio group and methylsulphonyl group. A protected hydroxy group $R_1$ of the compound of the general formula III is, for example, one of the groups mentioned in the foregoing.

The reaction according to the invention of compounds of the general formula II with compounds of the general formula III is performed, for example, at a temperature of between about 20° and 150° C in an inert organic solvent, and if necessary in a closed vessel. As solvents for reactions with compounds of the general formula III of which the hydroxy group is protected, it is possible to use, for example, nitriles such as acetonitrile, amides substituted in the amide group(s), such as N,N-dimethylformamide or N,N,N',N',N'',N''-hexamethylphosphoric acid triamide, hydrocarbons such as benzene or toluene, halogenated hydrocarbons such as methylene chloride or chloroform, ethereal solvents such as tetrahydrofuran or dioxane, or sulphoxides such as dimethylsulphoxide; and as solvents for reactions with the hydroxylamine embraced by the general formula III, it is possible to use in addition, in particular, lower alkanols such as methanol or ethanol. Within the above-mentioned temperature range, the reaction temperature for reactions with hydroxylamine is preferably in the lower to medium range, i.e. between about 20° and 90° C, and especially between 35° and 65° C, and the reaction temperature for the reactions with the other compounds of the general formula I is preferably in the medium range of about 50°–120°C, especially about 65°–105° C, and particularly at the boiling temperature of the employed solvent, if this temperature is in the last-mentioned range.

Partial reactions of compounds of the general formula II wherein X and Y are exchangeable radicals with the approximately equimolar amount of a compound of the general formula III are performed likewise in the above-stated solvents and temperature ranges, but if necessary nearer to the lower limits thereof. If X and Y are identical, then Y reacts first. The choice between a slight deficiency or excess of the compound to be reacted of the general formula III, relative to the compound of the general formula II, is governed by, inter alia, the reactivity of the starting materials, as well as by the possibilities of separation of starting materials, partial and complete reaction products, or the products resulting from these in a consequent reaction according to the invention.

The reaction of reaction products, following, if necessary, the main reaction according to the invention, in which reaction products one of the radicals X and Y, preferably X, is still an exchangeable group, such as a halogen atom, particularly chlorine, or a lower alkylthio or alkylsulphonyl group, especially the methylthio group or methylsulphonyl group, with a compound of the general formula III can be performed under the above-stated conditions of the main reactions. The reaction with ammonia to give corresponding compounds of the general formula I having an amino group $R_2$ is performed, for example, at temperatures of between about 130° and 200° C, preferably between 140° and 180° C, in an inert organic solvent, such as ethanol or methanol, and if necessary, that is, in most cases, in a closed vessel.

The hydrolysis of reaction products, likewise subsequent to the main reaction, in which products one of the radicals X and Y, preferably X, is still an exchangeable group, particularly a halogen atom, especially chlorine, to give corresponding compounds having a hydroxy group $R_2$, is performed, for example, at a temperature of between about 20 and 100° C in an alkaline medium, or, optionally, in an acid medium if $R_1$ is a hydroxy group or is to be in the final product. The hydrolysis is preferably carried out in a lower-alkanolic-aqueous alkali hydroxide solution, e.g. in a methanolic-aqueous or ethanolic-aqueous alkali hydroxide solution, or in an aqueous alkali hydroxide solution, particularly in a sodium or potassium hydroxide solution, at the boiling temperature thereof.

The liberation of a protected hydroxy group $R_1$ and of an optionally present, protected hydroxyamino group $R_2$, which follows, if required, the main reaction and, optionally, one of the aforementioned consequent reactions, is governed by the nature of the protective groups. Compounds of the general formula I which contain one or two protective groups that can be split in acid medium are treated, e.g. with highly diluted hydrochloric acid, e.g. with 0.5 to 2N, preferably with 1N, hydrochloric acid, at a temperature of between about 0° and 50° C, preferably at room temperature. Certain protected hydroxy groups can be quantitatively split also by treatment with aqueous acetic acid, e.g. 1-lower-alkoxy-ethoxy groups with 5% acetic acid at about 20° C and the 1,1,2,2-tetramethylpropyloxy group with 80% acetic acid on a boiling water bath, while the tert.butoxy group can be split, for example, with trifluoroacetic acid.

As a protected hydroxy group that can be split in a basic medium, the methoxyacetoxy group, for example, can be split with diluted aqueous ammonia solution at room temperature. This reaction may also be performed together with the aforementioned exchange of a group X or Y for ammonia, which requires more energetic conditions.

The hydrogenolysis of groups suitable for the purpose, particularly of monoarylmethoxy groups, such as the benzyloxy group, or of diarylmethoxy groups such as the diphenylmethoxy group, can be performed in the presence of the usual hydrogenation catalysts, for example, noble metal catalysts such as palladium on charcoal or platinum oxide, or in the presence of alloy-skeleton catalysts such as Raney nickel, in an inert organic solvent, such as dimethylformamide, methanol, ethanol or dioxane, at room temperature and normal pressure, or at moderately elevated temperatures and pressures, whereby the compound to be split can be used as such or as an acid addition salt, especially as hydrochloride.

Of the starting materials of the general formula II, some are known: see, e.g. U.S. Pat. No. 1,242,834 and German Auslegeschrift 1,103,931, as well as Dutch Patent Application 65,14743 (Chem. Abstr. 65, 10597e). Further compounds of the general formula II are obtainable by processes analogous to those for preparing known compounds, or by other processes known per se; e.g. compounds having a methylthio or methylsulphonyl group X and/or Y are prepared, for example, by reaction of corresponding chlorine compounds with metal-alkylmercaptides, particularly sodium or potassium alkylmercaptides, especially sodium methylmercaptide, in methanol or ethanol, at room temperature or at slightly elevated temperature, and, optionally, oxidation of the resulting alkylthio compounds, e.g. methylthio compounds, to methylsulphonyl compounds, for example, by means of peroxyacetic acid. Compounds of the general formula II having a lower alkylthio group, especially the methylthio group, as radical X can also be obtained by use of S-alkyl-isothioureas, particularly S-methyl-isothiourea, in ring-closure reactions as known per se.

A known starting material of the general formula III having a protected hydroxy group $R_1$ is O-(tetrahydropyran-2-yl-hydroxylamine (see 'Angew. Chem.' 78, 491 (1966). Further compounds of the general formula III can be prepared, for example, by causing N-hydroxyphthalimide, as the starting material, to undergo an addition reaction with vinyl ethers, or with analogous cyclic compounds such as ethyl vinyl ether, butyl vinyl ether, 4-methoxy-5,6-dihydro-2H-pyrane, -2H-thiopyrane or -2H-thiopyrane-1,1-dioxide; or by reaction of N-hydroxyphthalimide with 1,1,2,2-tetramethylpropyl chloride, or acylation thereof with methoxyacetic acid anhydride; and, in all cases, subsequent hydrazinolysis of the resulting O-derivative of N-hydroxyphthalimide.

The present invention relates also to such modifications of the process of the invention, of consequent reactions of the process and of preliminary stages thereof, whereby the process is interrupted at some stage, or whereby a compound occurring as intermediate at some stage is used as starting material and the uncompleted steps are performed, or whereby a starting material is formed under the reaction conditions, or, optionally, is used in the form of a salt. If the required starting materials are optically active, then both the racemate and the isolated antipodes can be used. Also such starting materials can optionally be used in the form of salts. If final materials are obtained as racemates or mixtures of racemates, then these can, within the scope of the present invention, be optionally separated and split up into their antipodes.

Depending on the conditions of the process and the starting materials, the products of the process are obtained in the free form or as hydrates, or in the form of their acid addition salts which is likewise embraced by the invention, or optionally also as hydrates of the last-mentioned. The acid addition salts of the new compounds of the general formula I can be converted, in a manner known per se, into the free bases, e.g. with basic agents, such as alkalies or ion exchangers. Alternatively, the compounds of the general formula I obtained according to the invention can optionally be converted, in the usual manner, into their addition salts with inorganic or organic acids. For example, the acid desired as salt component is added to a solution of a compound of the general formula I in an organic solvent. The organic solvents preferably chosen for the reaction are those in which the resulting salt is difficultly soluble, so that it can be separated by filtration. Such solvents are, for example, ethyl acetate, methanol, ether, acetone, methyl ethyl ketone, acetone/ether, acetone/ethanol, methanol/ether or ethanol/ether.

Instead of free bases, pharmaceutically acceptable acid addition salts can be used as pharmaceutical active substances, that is to say, salts with such acids of which the anions are not toxic in the dosage amounts concerned. Furthermore, it is advantageous if the salts to be used as pharmaceutical active substances crystallise well and are not, or only slightly, hygroscopic. For salt formation with compounds of the general formula I, it is possible to use, for example, hydrochloric acid, hydrobromic acid, sulphuric acid, phosphoric acid, methane-sulphonic acid, ethanesulphonic acid, 2-hydroxyethane-sulphonic acid, acetic acid, lactic acid, succinic acid, fumaric acid, maleic acid, malic acid, tartaric acid, citric acid, benzoic acid, salicyclic acid, phenylacetic acid, mandelic acid and embonic acid.

The new pyrimidine derivatives of the general formula I and their acid addition salts possess valuable biological properties; they are, in particular, antibacterially effective and they potentiate the antibacterial action of derivatives of sulphanilamide. The antibacterial effectiveness of compounds of the general formula I and of their pharmaceutically acceptable acid addition salts, e.g. of 2-amino-4-(hydroxyamino)-5-(3,4,5-trimethoxybenzyl)-pyrimidine, can be demonstrated, for example, by oral administration of doses of 100–250 mg/kg daily to mice infected with Escherichia coli. Likewise identifiable is a distinct synergism with sulphanilamide derivatives. The pyrimidine derivatives of the general formula I can be used on their own or, in particular, in combination with sulphanilamide derivatives, such as sulphadiazine, sulphamerazine, sulphisomidine, sulphaphenazole, sulphachloropyridazine, sulphaperine, sulphadimethoxine, sulphadoxine, sulphalene, sulphamethoxydiazine, sulphamethoxazole, $N^1$-(6-cyclopropyl)-4-pyrimidinyl)-sulphanilamide, $N^1$-(6-cyclopropyl-5-methoxy-4-pyrimidinyl)-sulphanilamide and $N^1$-[2-(methoxymethyl)-6-methoxy-4-pyrimidinyl)]-sulphanilamide for the treatment of bacterial infectious diseases in warm-blooded animals, preferably by oral administration. The mixture ratio of pyrimidine derivative of the general formula I to sulphanilamide derivative is preferably between about 1:2 and about 1:10, depending on intensity and duration of action of the sulphanilamide derivative used, and in particular it is about 1:5. In the case of larger mammals, the daily dose is, after a higher initial dose if necessary, preferably 2–10 mg/kg of pyrimidine derivative of the general formula I, and 4–40 mg/kg of sulphanilamide derivative or 6–48 mg/kg of a synergistic mixture.

In addition, the compounds of the general formula I and their acid addition salts have an antimalarial action according to tests on mice infected with Plasmodium berghei, and on monkeys infected with P. cynomolgi or P. knowlesi. Thus, for example, in the case of mice infected with P. berghei, the $ED_{50}$ of 2-amino-4-(hydroxyamino)-5-(p-chlorophenyl)-6-ethyl-pyrimidine-hydrochloride is 4 × 0.25 mg/kg orally and subcutaneously, and the curative dosage amount of the same compound is 4 × 1 to 3 mg/kg orally and subcutaneously. At the same time, the compounds of the general formula I and their pharmaceutically acceptable acid addition salts, such as the aforementioned hydrochloride, have a low toxicity.

Also in the case of plasmodia, the compounds of the general formula I, such as the aforementioned hydrochloride, potentiate the action of sulphanilamide derivatives, for example of the active substances specifically mentioned in the foregoing. The compounds of the general formula I and their pharmaceutically acceptable acid addition salts can be used on their own as well as in combination with sulphanilamide derivatives, e.g. with the aforementioned, as antimalarial active substances, particularly for the prophylaxis of malaria, and also for the treatment of toxoplasmosis. The doses are preferably between 0.2 and 1.0 mg/kg per day; with administration of the active substances for the prophylaxis of malaria being effected at intervals of several days, particularly once weekly. The compounds of the general formula I and their acid addition salts are orally administered on their own or together with other antimalarial active substances, especially together with approximately the 2- to 10-fold, preferably 5-fold, amount of one of the aforementioned sulphanilamide derivatives, either in combined or in separate dosage units.

The invention relates particularly to pyrimidine derivatives of the general formula I wherein $R_1$, $R_2$ and $R_4$ have the meanings given under formula I, and $R_3$ denotes a phenyl radical or a phenylalkyl radical having at most 4 carbon atoms in the alkyl moiety, which radicals are at most tri-substituted by substituents from the series of halogen atoms up to atomic number 35, alkyl, alkoxy or 1-hydroxyalkyl groups having at most 4 carbon atoms, hydroxy groups, trifluoromethyl groups and methylenedioxy groups. The invention relates more particularly to pyrimidine derivatives of the general formula I wherein $R_1$ represents the hydroxy or tetrahydropyran-2-yloxy group, $R_2$ represents the amino, hydroxyamino [[(tetrahydropyran-2-yloxy)-amino] group, $R_3$ represents a phenyl or benzyl group at most trisubstituted by substituents from the series of halogen atoms up to atomic number 35, alkyl, alkoxy or 1-hydroxyalkyl groups having at most 4 carbon atoms, hydroxy groups, trifluoromethyl groups and methylenedioxy groups, whereby at most two hydroxy groups or trifluoromethyl groups, or at most one methylenedioxy group, are present, on their own or in addition to any of the other above-mentioned substituents, and $R_4$ represents hydrogen or a methyl or ethyl group.

The invention relates above all to pyrimidine derivatives of the general formula I wherein $R_1$ represents the tetrahydropyran-2-yloxy group or benzyloxy group and especially the hydroxy group, $R_2$ represents the [(tetrahydropyran-2-yloxy)-amino] group and, in particular, the amino or hydroxyamino group, $R_3$ represents a phenyl or benzyl group at most tri-substituted by substituents from the series of chlorine atoms, methoxy and hydroxy groups, wherein, however, at most two hydroxy groups are present, on their own or together with other substituents, and $R_4$ represents hydrogen or a methyl or ethyl group. The invention relates first of all to compounds of the general formula I wherein $R_1$, $R_2$, $R_3$ and $R_4$ have the meanings defined immediately above, the group $R_1$-NH is in the 4-position and the group $R_2$ is in the 2-position.

The invention relates especially to the pyrimidine derivatives of the general formula I which are mentioned in the Examples, particularly 2-amino-4-(hydroxyamino)-5-(3,4,5-trimethoxybenzyl)-pyrimidine and 2-amino-4-(hydroxyamino)-5-(p-chlorophenyl)-6-ethyl-pyrimidine, and to their pharmaceutically acceptable acid addition salts, such as the hydrochlorides.

The pyrimidine derivatives of the general formula I and their pharmaceutically acceptable acid addition salts are administered, on their own or in combination with antibacterial sulphanilamide derivatives, preferably orally or optionally rectally, either as dosage units, such as tablets, dragees, capsules or suppositories, or as preparations not divided into dosage units, particularly in the form of syrups. The preparations mentioned can contain the usual diluting agents and/or carriers, and are prepared in a manner known per se. Dosage units for oral administration contain, for example, 20 to 100 mg of a pyrimidine derivative of the general formula I and 50 to 500 mg of a sulphanilamide derivative. Syrups contain, for example, the same amounts or half the amounts of the two active substances in 5 ml.

The following examples further illustrate the preparation of tablets:

a. 2000 g of sulphadiazine, 400 g of 2-amino-4-(hydroxyamino)-5-(3,4,5-trimethoxybenzyl-pyrimidine, 260 g of maize starch and 260 g of lactose are thoroughly mixed. The resulting mixture is further mixed with 60 g of glycerin and a solution of 100 g of gelatine in distilled water and the whole is kneaded for 20 minutes. The moist mixture, now homogeneous, is granulated through a 25-mesh (per cm$^2$) sieve and then dried. The dried granulate is passed through a 60-mesh (per cm$^2$) sieve, and subsequently mixed for one hour with 150 g of potato starch, 150 g of talcum and 20 g of magnesium stearate. The resulting mixture is pressed to obtain 10,000 tablets each weighing 340 mg and each containing 200 mg of sulphadiazine and 40 mg of 2-amino-4-(hydroxyamino)-5-(3,4,5-trimethoxybenzyl)-pyrimidine.

Instead of sulphadoazine, it is possible to use, for example, the same amount of sulphamethoxazole.

b. 250 g of 2-amino-4-(hydroxyamino)-5-(p-chlorophenyl)-6-ethyl-pyrimidine-hydrochloride is mixed with 175.80 g of lactose and 169.70 g of potato starch; the mixture is moistened with an alcoholic solution of 10 g of stearic acid, and granulated through a sieve. The resulting granulate is dried and there are then added to it 160 g of potato starch, 200 g of talcum, 2.50 g of magnesium stearate and 32 g of colloidal silicon dioxide; the mixture is pressed to obtain 10,000 tablets each weighing 100 mg and each containing 25 mg of active substance.

The following examples illustrate the preparation of pyrimidine derivatives of the general formula I; the examples are however not intended in any way to limit the scope of the invention. Temperatures are given in degrees Centigrade.

EXAMPLE 1

7.6 g of 2-amino-4-chloro-5-(3,4,5trimethoxybenzyl)-pyrimidine and 6.5 g of 0-(tetrahydropyran-2-yl)-hydroxylamine are refluxed for 12 hours in 170 ml of acetonitrile. A slight precipitate is removed by filitration with suction and the acetonitrile is distilled off. The residue is purified by chromatography on neutral aluminium oxide with the use of methylene chloride as solvent and eluant. The resulting 2-amino-4-[(tetrahydropyran-2-yloxy)-amino]-5-(3,4,5-trimethoxybenzyl)-pyrimidine-hydrate melts at 75°–80°.

EXAMPLE 2

6 g of 2-amino-4-[(tetrahydropyran-2-yloxy)-amino]-5-(3,4,5-trimethoxybenzyl)-pyrimidine-hydrate is stirred in 40 ml of 1N hydrochloric acid for 15 minutes at room temperature. The pH-value is then adjusted to 7 with 1N sodium hydroxide solution. The precipitated 2-amino-4-(hydroxyamino)-5-(3,4,5trimethoxybenzyl)-pyrimidine is filtered off under suction and recrystallised from butanol, M.P. 208°–210°.

EXAMPLE 3

6 g of 2,4-dichloro-5-(3,4,5-trimethoxybenzyl)-pyrimidine and 11.7 g of 0-(tetrahydropyran-2-yl)-hydroxylamine are refluxed for 12 hours in 50 ml of acetonitrile. After cooling, the reaction mixture is filtered off with suction from a slight precipitate; the filtrate is concentrated in vacuo and the residue is taken up in methylene chloride, washed with water and dried. The methylene chloride phase is absorbed onto neutral aluminium oxide as the adsorbent. Eluting with methylene chloride yields, after first runnings containing unreacted chlorine compound, 2,4-bis-[(tetrahydropyran-2-yloxy)-amino]-5-(3,4,5-trimethoxybenzyl)-pyrimidine, which does not crystallise.

EXAMPLE 4

3.8 g of 2,4-bis-[(tetrahydropyran-2-yloxy)-amino]-5-(3,4,5-trimethoxybenzyl)-pyrimidine is stirred in 30 ml of 1N hydrochloric acid for 10 minutes at room temperature. The reaction mixture is then neutralised with 1N sodium hydroxide solution and the precipitating oil is taken up in methylene chloride. Chromatography on silica gel with the use of methylene chloride as eluant yields 2-[(tetrahydropyran-2-yloxy)-amino]-4-(hydroxyamino)-5-(3,4,5-trimethoxybenzyl)-pyrimidine, M.P. 190°–192°.

EXAMPLE 5

3 g of 2-amino-4-chloro-5-(3,4,5-trimethoxybenzyl)-pyrimidine is added to a methanolic hydroxylamine solution prepared from 1.4 g of hydroxylamine-hydrochloride, 0.46 g of sodium and 50 ml of absolute methanol. The mixture is stirred for 48 hours at 40°; it is subsequently concentrated in vacuo and the residue is recrystallised from butanol to obtain 2-amino-4-(hydroxyamino)-5-(3,4,5-trimethoxybenzyl)-pyrimidine, M.P. 208°–210°, which is identical to the product described in Example 2.

EXAMPLE 6

7.6 g of 2-amino-4-chloro-5-(3,4,5-trimethoxybenzyl)-pyrimidine and 6.7 g of 0-benzyl-hydroxylamine are refluxed in 100 ml of acetonitrile for 12 hours. The reaction mixture is cooled and 2-amino-4-(benzyloxyamino)-5-(3,4,5-trimethoxybenzyl)-pyrimidine-hydrochloride precipitates. It is separated by filtration under suction and melts at 272° after recrystallisation from dimethylformamide.

EXAMPLE 7

1 g of 2-amino-4-(benzyloxyamino)-5-(3,4,5-trimethoxybenzyl)-pyrimidine-hydrochloride is dissolved in 100 ml of warm dimethylformamide, and hydrogenated under hydrogen at normal pressure, at room temperature, in the presence of 100 mg of 5% palladium charcoal catalyst. The catalyst is then filtered off and the filtrate is concentrated in vacuo. The residue is suspended in 1N sodium hydroxide solution, whereupon 2-amino-4-(hydroxyamino)-5-(3,4,5-trimethoxybenzyl)-pyrimidine precipitates in crystalline form. It is filtered off with suction and recrystallised from butanol, M.P. 208°–210°. It is identical to the product described in Example 2.

EXAMPLE 8

17.5 g of 2-amino-4-chloro-5-(p-chlorophenyl)-6-ethyl-pyrimidine and 18.6 g of 0-(tetrahydropyran-2-yl)-hydroxylamine is refluxed in 400 ml of acetonitrile for 12 hours. The reaction mixture is filtered and the filtrate is concentrated in vacuo. The oily residue is taken up in ether, whereupon 2-amino-4-[(tetrahydropyran-2-yloxy)-amino]-5-(p-chlorophenyl)-6-ethyl-pyrimidine-hydrochloride crystallises out. For conversion into the free base, 5.0 g of crude hydrochloride is distributed between dilute sodium hydroxide solution and chloroform. The chloroform phase is washed with water, dried by means of magnesium sulphate and concentrated in vacuo. After recrystallisation from ethanol, the resulting 2-amino-4-[(tetrahydropyran-2-yloxy)-amino]-5-(p-chlorophenyl)-6-ethyl-pyrimidine melts at 200°–202°.

EXAMPLE 9

12 g of crude 2-amino-4-[(tetrahydropyran-2-yloxy)-amino]-5-(p-chlorophenyl)-6-ethyl-pyrimidine-hydrochloride is stirred in 100 ml of 1N hydrochloric acid for 5 minutes at 40° and for one hour at room temperature. The precipitated product is filtered off, washed with water and dried in a stream of air. After recrystallisation from ethanol/ether, the resulting 2-amino-4-(hydroxyamino)-5-(p-chlorophenyl)-6-ethyl-pyrimidine-hydrochloride melts at 294° with decomposition.

What we claim is:
1. A pyrimidine of the formula I

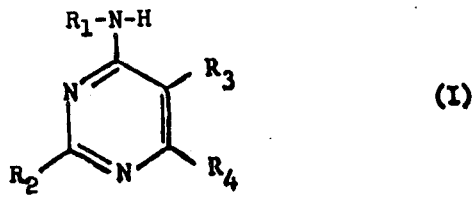

(I)

wherein
$R_1$ represents hydroxy, benzyloxy or tetrahydropyran-2-yloxy,
$R_2$ represents amino or,
$R_3$ represents phenyl, benzyl, phenyl or benzyl which are mono-or trisubstituted by a member selected from the group consisting of chlorine and methoxy,
$R_4$ represents hydrogen, methyl, or ethyl and their pharmaceutically acceptable addition salts with inorganic and organic acids.

2. A compound according to claim 1, which is 2-amino-4-(hydroxyamino)-5-(3,4,5-trimethoxybenzyl)-pyrimidine.

3. A compound according to claim 1, which is 2-amino-4-[(tetrahydropyran-2-yloxy)-amino]-5-(3,4,5-trimethoxybenzyl)-pyrimidine and its hydrate.

4. A compound according to claim 1, which is 2,4-bis-[(tetrahydropyran-2-yloxy)-amino]-5-(3,4,5-trimethoxybenzyl)-pyrimidine.

5. A compound according to claim 1, which is 2-[(tetrahydropyran-2-yloxy)-amino]-4-(hydroxyamino)-5-(3,4,5-trimethoxybenzyl)-pyrimidine.

6. A compound according to claim 1, which is 2-amino-4-(benzyloxyamino)-5-(3,4,5-trimethoxybenzyl)-pyrimidine and its hydrochloride.

7. A compound according to claim 1, which is 2-amino-4-(hydroxyamino)-5-(p-chlorophenyl)-6-ethyl-pyrimidine and its hydrochloride.

8. A compound according to claim 1, which is 2-amino-4-[tetrahydropyran-2-yloxy)-amino]-5-(p-chlorophenyl)-6-ethyl-pyrimidine and its hydrochloride.

* * * * *